United States Patent
Karr

(10) Patent No.: US 8,504,164 B2
(45) Date of Patent: Aug. 6, 2013

(54) LOW ENERGY COMMUNICATIONS FOR IMPLANTED MEDICAL DEVICES

(76) Inventor: Lawrence J. Karr, Santa Monica, CA (US)

(*) Notice: Subject to any disclaimer, the term of this patent is extended or adjusted under 35 U.S.C. 154(b) by 243 days.

(21) Appl. No.: 13/086,922

(22) Filed: Apr. 14, 2011

(65) Prior Publication Data

US 2011/0257706 A1    Oct. 20, 2011

Related U.S. Application Data

(60) Provisional application No. 61/323,930, filed on Apr. 14, 2010.

(51) Int. Cl.
*A61N 1/18* (2006.01)
(52) U.S. Cl.
USPC .............................. 607/60; 331/66; 331/154
(58) Field of Classification Search
None
See application file for complete search history.

(56) References Cited

U.S. PATENT DOCUMENTS

| 2006/0064037 A1* | 3/2006 | Shalon et al. | 600/586 |
| 2009/0112288 A1 | 4/2009 | Hur et al. | |

OTHER PUBLICATIONS

Lavasani, H. et al., A 145MHz Low Phase-Noise Capacitive Silicon Micromechanical Oscillator, *IEEE International Electron Devices Meeting*, p. 675-678, Dec. 2008.

* cited by examiner

*Primary Examiner* — Brian T Gedeon
*Assistant Examiner* — Ankit Tejani
(74) *Attorney, Agent, or Firm* — Gifford, Krass, Sprinkle, Anderson & Citkowski, P.C.

(57) ABSTRACT

Techniques are generally described for low average power communications that can be used for communications between one or more bionic implants and/or one or more control units. Bionic implants and/or control units can be adapted to provide stimulus control and/or sensory or other feedback back from the bionic implants. An example system may include implant devices configured to exchange brief messages between other devices. Some examples may rely on coarse message timing that can be derived from a quartz tuning fork type of resonator. Carrier frequency control can be derived from an on-chip MEMS resonator adapted for high frequency use. An electrical stimulation power supply in each implant can be configured for use in nerve/muscle excitation and/or as a polarizing voltage source for the MEMS resonator. Various compensation mechanisms are described that can be used to compensate for the imprecise and/or temperature dependent frequency in the MEMS resonator.

20 Claims, 7 Drawing Sheets

LOW ENERGY COMMUNICATIONS FOR IMPLANTED MEDICAL DEVICES

REFERENCE TO RELATED APPLICATION

This application claims priority from U.S. Provisional Patent Application Ser. No. 61/323,930, filed Apr. 14, 2010, the entire content of which is incorporated herein by reference.

FIELD OF INVENTION

A low average power communication system is generally described that can be used for communications between one or more bionic implants and/or one or more control units to provide stimulus control and/or sensory or other feedback back from the bionic implants.

BACKGROUND OF THE INVENTION

Unless otherwise indicated herein, the materials described in this section are not prior art to the claims in this application and are not admitted to be prior art by inclusion in this section.

Various methods may be used in implanted bionic devices to minimize power consumption. In some examples, some variety of time division multiplexing (i.e., time slotting) such as TDMA (time-division-multiple-access) scheme can be employed with pre-arranged synchronization between implants and non-implanted devices. In some cases, implants can be inductively powered by RF fields. In other cases, timeslots can be assigned to implants, and brief messages can be exchanged between the implants and the control units with some variety of communication that occurs at a regular cadence. The implants may be configured to rely on internal time constants such as resistor-capacitor based timing (i.e., RC timing), which may necessarily use very inefficient signaling means since time and frequency needs to be well known for most modern communication schemes.

In some cases a quartz crystal can be used as part of a time base circuit in an implant device. In such cases, the implant device's timing circuits may be implemented in a number of schemes such as a tuning fork or a shear mode resonator type of timing scheme. A typical tuning fork scheme using a quartz crystal may operate with a frequency of about 32,768 Hz. At these types of frequencies, a typical implant may use power on the order of nano-watts, but the implant may not provide an appropriate reference frequency for use with VHF/UHF transceivers, whose synthesizers typically may require more rapid updates.

The communication and time-keeping power requirements of tiny implanted devices may determine their useful battery life. For example, some of the power consumed in an implant device is determined by the transmit/receive power required for operation at the specified carrier frequencies, while additional power consumption requirements may be determined by the regularity or irregularity (i.e., intermittent periodicity) of communications.

Some implantable electronic medical devices may operate without the benefit of a quartz crystal. Unfortunately, since communications generally require both accurate scheduling and accurate frequency control, these types of implant devices may generally be unable to support efficient communications.

Some attempts have been made with inductively powered implant devices that use either the frequency of the inductive power or a multiple or integer fraction of the power frequency as a time base. Although these designs may be functional, such designs are typically very limited in capabilities, and cannot be practically used. For example, an inductively powered implant device may not be used at multiple locations on a patient, and may require wearing inductive power sources.

Some implantable devices may be configured to use shear mode quartz crystals with resonant frequencies in the MHZ range. In time base circuits (e.g., oscillators), these shear mode quartz crystal devices may require significant minimum operating currents to maintain oscillation (e.g., on the order of a few micro-amps). When such time base circuits are operated from low power, they may produce noisy clock signals that can adversely impact various circuits in the implant. In addition, the tiny sizes required for implantation may necessitate the use of tiny "strip" type resonator circuits such as AT cut quartz crystal strip resonators. Such small scale strip type resonators typically exhibit modest Q values compared to larger quartz resonators. The present disclosure appreciates that it may be difficult to achieve satisfactory time bases in implant devices that use miniature strip resonator topologies such as AT cut quartz crystal oscillators.

In some examples, a watch crystal (e.g., a quartz crystal) can be utilized in a tuning fork resonator type of time base circuit. One problem with the simple use of a watch crystal is that high resolution timing may not be supported by the use of such a time-base. If a tuning fork resonator is used as the frequency reference of a VHF or UHF radio transceiver, then the update rate will be slow and therefore the loop bandwidth will be small for any phase locked loop circuits that may be built using the tuning fork as a reference. In this case, phase noise performance at radio frequencies will be mediocre, and synthesizers start up and settling times will be long, of the order of milliseconds at least. This long settling time makes it difficult to operate the radio communications parts of the bionic implant efficiently in a short burst.

Micro-Electro-Mechanical System (i.e., MEMS) type resonators may be desirable in very small devices, since they are very small and may even be constructed as part of an integrated circuit that may be used for other purposes. The present disclosure appreciates that there are several difficulties associated with MEMS type of resonators.

In some examples a MEMS type of resonator may be built on silicon. One problem appreciated in the present disclosure is that the resonant frequency for a MEMS type of resonator built as parts of an integrated circuit tends to have a large temperature coefficient. The temperature coefficient is largely a consequence of the fact that the MEMS resonator will typically be built from silicon, where silicon has a large temperature coefficient of mechanical modulus. This temperature coefficient makes MEMS resonators difficult to use as accurate timing or frequency sources even given the narrow temperature range expected in a bionic implant.

In some additional examples, a MEMS resonator may be built on silicon without the use of a piezoelectric material. This type of MEMS resonator may need significant polarizing voltages to achieve reasonable electromechanical coupling coefficients.

In some further examples, a silicon based MEMS resonator such as silicon bulk acoustic resonators (i.e., SiBAR) uses the thickness mode, which may have desirably high Q values but also can result in the generation of low phase noise signals. An example SiBAR device is described by H. M Lavasani, A. K. Samarao, G. Casinovi and F. Ayazi in "A 145 MHz Low Phase-Noise Capacitive Silicon Micromechanical Oscillator", *IEEE International Electron Devices Meeting*, pp. 675-678, December 2008; which is hereby incorporated by reference in its entirety.

SUMMARY OF THE INVENTION

This invention relates to low average power communication systems applicable to one or more bionic implants communicating with one or more control units to provide stimulus control and/or sensory or other feedback signals.

An implanted medical device constructed in accordance with the invention includes a low frequency quartz oscillator circuit operative to generate a low frequency clock signal and a sleep timer circuit configured to periodically activate the implanted medical device from a sleep mode to an active mode. A MEMS resonator circuit having a characteristic resonant frequency is operative to generate an oscillator signal when the implanted medical device is operated in the active mode. The oscillator signal has a reference frequency corresponding to the characteristic resonant frequency of the MEMS resonator.

A frequency compensated digital oscillator is selectively operated with the oscillator signal from the MEMS oscillator circuit when the implanted medical device is operated in the active mode. The frequency compensated digital oscillator is configured to provide carrier frequency control and precision timing for the RF communication circuit using the measured frequency error of the reference frequency relative to the low frequency clock signal from the low frequency quartz oscillator circuit without frequency adjustment of the oscillator signal.

In the preferred embodiments the MEMS oscillator is an on-chip silicon MEMS resonator and the low frequency quartz oscillator is a quartz tuning fork resonator. The carrier frequency associated with the radio frequency communications may be in a range from about 100 MHz to about 3000 MHz. The sleep timer may be configured to intermittently operate the radio frequency communications to conserve energy.

The implanted medical device may include a capacitive and/or inductive voltage multiplier adapted to deliver therapy to a nerve or tissue of a patient. The implanted medical device may further include a charge pump circuit and a polarizing voltage source circuit, wherein the charge pump circuit is configured to generate an increased voltage signal when the implanted medical device is operated in the active mode, wherein the increased voltage signal is used to deliver therapy to a nerve or tissue of a patient, and wherein the polarizing voltage source is adapted to power the MEMS resonator circuit using the same increased voltage signal that is used for patient therapy. The implanted medical device may further comprise a neural stimulator circuit that is powered by the increased voltage signal from the charge pump circuit, wherein the neural stimulator circuit is configured to deliver therapy to a nerve or tissue of a patient when the implanted medical device is operated in an active mode.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified. All figures are configured in accordance with at least some embodiments of the present disclosure.

DETAILED DESCRIPTION OF THE PRESENT INVENTION

Figure 1:
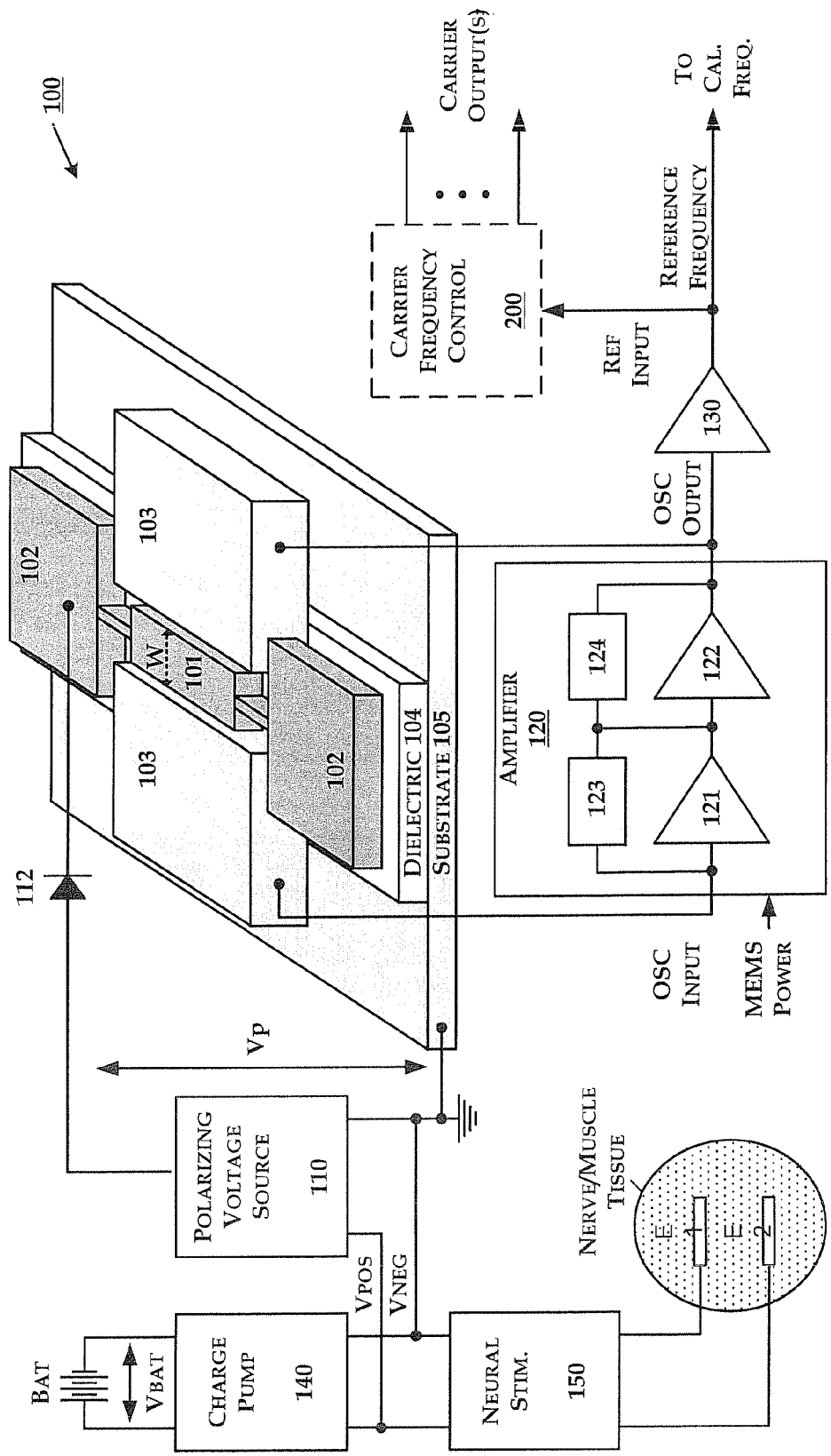
FIG. 1 shows the cross-section of an example MEMS resonator configured for use as an oscillator (e.g., VHF/UHF frequencies) and a carrier frequency controlling element.

Various embodiments will be described in detail with reference to the drawings, where like reference numerals represent like parts and assemblies throughout the several views. References to various embodiments do not limit the scope of the invention, which is limited only by the scope of the claims attached hereto. Additionally, any examples set forth in this specification are not intended to be limiting and merely set forth some of the many possible embodiments for the claimed invention.

Throughout the specification and claims, the following terms take at least the meanings explicitly associated herein, unless the context clearly dictates otherwise. The meanings identified below are not intended to limit the terms, but merely provide illustrative examples for use of the terms. The meaning of "a," "an," and "the" may include reference to both the singular and the plural. The meaning of "in" may include "in" and "on." The term "connected" may mean a direct electrical, electro-magnetic, mechanical, logical, or other connection between the items connected, without any electrical, mechanical, logical or other intermediary items. The term "coupled" can mean a direct connection between items, an indirect connection through one or more intermediaries, or communication between items in a manner that may not constitute a physical connection. The term "circuit" can mean a single component or a plurality of components, active and/or passive, discrete or integrated, that are coupled together to provide a desired function. The term "signal" can mean at least one current, voltage, charge, data or other such identifiable quantity including electrically coupled and magnetically coupled signals.

Briefly stated, the present disclosure generally relates to methods, devices and systems for low average power communications. Various techniques described herein can be used for communications between one or more bionic implants and/or one or more control units. The bionic implants and/or control units can be adapted to provide stimulus control and/or sensory or other feedback back from the bionic implants. An example system may include implant devices that can be configured to exchange brief messages between other implant devices or some other type of device. Some example communication systems may rely on coarse message timing that can be derived from a quartz tuning fork type of resonator. Carrier frequency control can be derived from an on-chip MEMS type of resonator adapted for use in a high frequency oscillator circuit. An electrical stimulation power supply in each implant can be configured for use in nerve/muscle excitation and/or configured for use as a polarizing voltage source for the MEMS resonator. Various compensation mechanisms are described that can be used to compensate for the imprecise and/or temperature dependent frequency in the MEMS resonator.

FIG. 1 shows the cross-section of an example MEMS resonator 100 configured for use as an oscillator (e.g., VHF/UHF frequencies) and for use as a carrier frequency controlling element, arranged in accordance with at least some embodiments of the present disclosure. As illustrated, a MEMS resonator 100 can be constructed as a width extensional mode resonator. The MEMS resonator includes a central bar portion 101 that is supported at opposite ends by supporting portions 102. The central bar portion 101 has a width of W, a length of L, and a thickness of T. The bar portion 101 is electro-statically coupled to a pair of electrodes 103, which are each separated from the central bar portion by a capacitive gap.

The extensional width resonator can be built on an insulating material 104 on a substrate 105 so that it can be electrically coupled to a polarizing voltage source 110. The insulating substrate might be any appropriate dielectric material that is suitable as an insulator such as, for example, a layer of quartz or sapphire. The electrodes 103, which may be comprised of heavily doped silicon, can be coupled to the input and output of an amplifier 120, which is configured to provide enough gain to achieve oscillation. Amplifier 120 can be comprised of a two-stage amplifier circuit, which may include a first amplifier 121 and a second amplifier 122. The first amplifier may, for example, be comprised of a trans-impedance amplifier with an adjustable gain via a first feedback circuit 123. In some examples, the first feedback circuit 123 may be a variable resistance circuit that is configured to vary the gain of the first stage amplifier 121 in response to varying the resistance of the first feedback circuit 123. The second amplifier 122 may, for example, be comprised of a voltage amplifier with an adjustable amount of feedback via a second feedback circuit 124, which may also be a variable resistance circuit. In some examples, the voltage amplifier is configured to provide both gain and a 180 degree phase-shift. Since the amplifier 120 and the MEMS device can both be manufactured on silicon, a complete oscillator may be realized on a single semiconductor substrate 105, making the assembly extremely compact.

The output of the amplifier circuit 120 can be coupled to a buffer circuit 130 that is adapted to receive the oscillator signal from the output of amplifier 120 and provide a buffered oscillator signal to the carrier frequency control circuit 200. In some examples, the buffer circuit 130 is configured to provide a buffered oscillator signal with unity gain, either inverting or non-inverting as may be required. In some additional examples, the buffer circuit 130 may be configured to provide additional gain or attenuation to the oscillator signal from amplifier 120 to provide either an attenuated or gained oscillator signal. The reference frequency associated with the oscillator output can be calibrated for use in transmitter and/or receiver applications such as radio frequency communications (e.g., RF, UHF, VHF, etc.) that may be required between a medical implant device and some other remote device or external unit. In some examples, the radio frequency communications may be in a range from about 100 MHz to about 3000 MHz.

The resonator bar portions 101 and 102 in the MEMS resonator are located on an insulator material such as a dielectric (e.g., quartz), which is in turn located on a relatively conductive substrate material 104 (e.g., silicon). The bar portions 101 and 102 of the MEMS device have relatively large areas that operate as a first capacitive plate, while the substrate 104 operates as a second capacitive plate. With the insulator material 103 located between the bar portions 101 and 102 of the resonator and the substrate material 104, a fairly significant low loss capacitor is formed. The polarizing voltage source 110 is configured to couple a polarizing bias signal to the bar portions 101, 102 of the MEMS device 100, where charge be stored in the capacitor formed between the substrate 104 and the bar portions 101 and 102 of the MEMS device. To prevent charge from being lost when the polarizing voltage is diminished or discharged, a diode 112 or some other similar switch device can be series coupled between the polarizing voltage source 110 and the MEMS device 100.

FIG. 1 also shows a neural stimulator circuit 150 that is adapted to deliver charge to surrounding nerve/muscle tissue via one or more electrodes E1, E2. The neural stimulator can be battery powered by a battery BAT with a relatively low voltage Vbat, and thus may require charge pump circuit 140 to develop a sufficient voltage, charge and/or current to deliver stimulation signals to the electrodes (E1, E2) that are sufficient for neural stimulation. Neural stimulation may require voltages above about 9V nominally, for example. In some examples the battery voltage (VBat) may be in a range from about 1V to about 5V. For example, a lithium battery could be used that has a voltage in a range from about 1.5V to about 3.7V, with some examples having a voltage of nominally about 3V. For an example lithium battery with a nominal voltage of 3V, the increased voltage produced by the charge pump circuit 140 may be in a range from about 6V to about 24V. In such examples, the charge pump circuit 140 may be configured to multiply the battery voltage by a multiplication factor of 2×, 3×, 4×, 5×, 6×, 8×, 9×, etc., corresponding to the increased voltages on the order of 6V, 9V, 12V, 15V, 18V, 21V and 24V, respectively. These increased voltages can be used to deliver stimulation current or charge for neural stimulation. In some examples, the charge and current that is delivered for neural stimulation may be on the order of micro-coulombs ($\mu C$) or micro-amperes ($\mu A$).

The polarizing voltage source 110 can be provided power from any appropriate power source such as battery BAT. In some examples, the charge pump circuit 140 can be coupled to the polarizing voltage source 110 such that the polarizing source 110 can be powered by the increased voltages (VPos, VNeg). In such examples, the polarizing voltage VP that is coupled to the MEMS resonator 100 is based on the increased power supply voltages from the output of the charge pump circuit 140.

Figure 2:
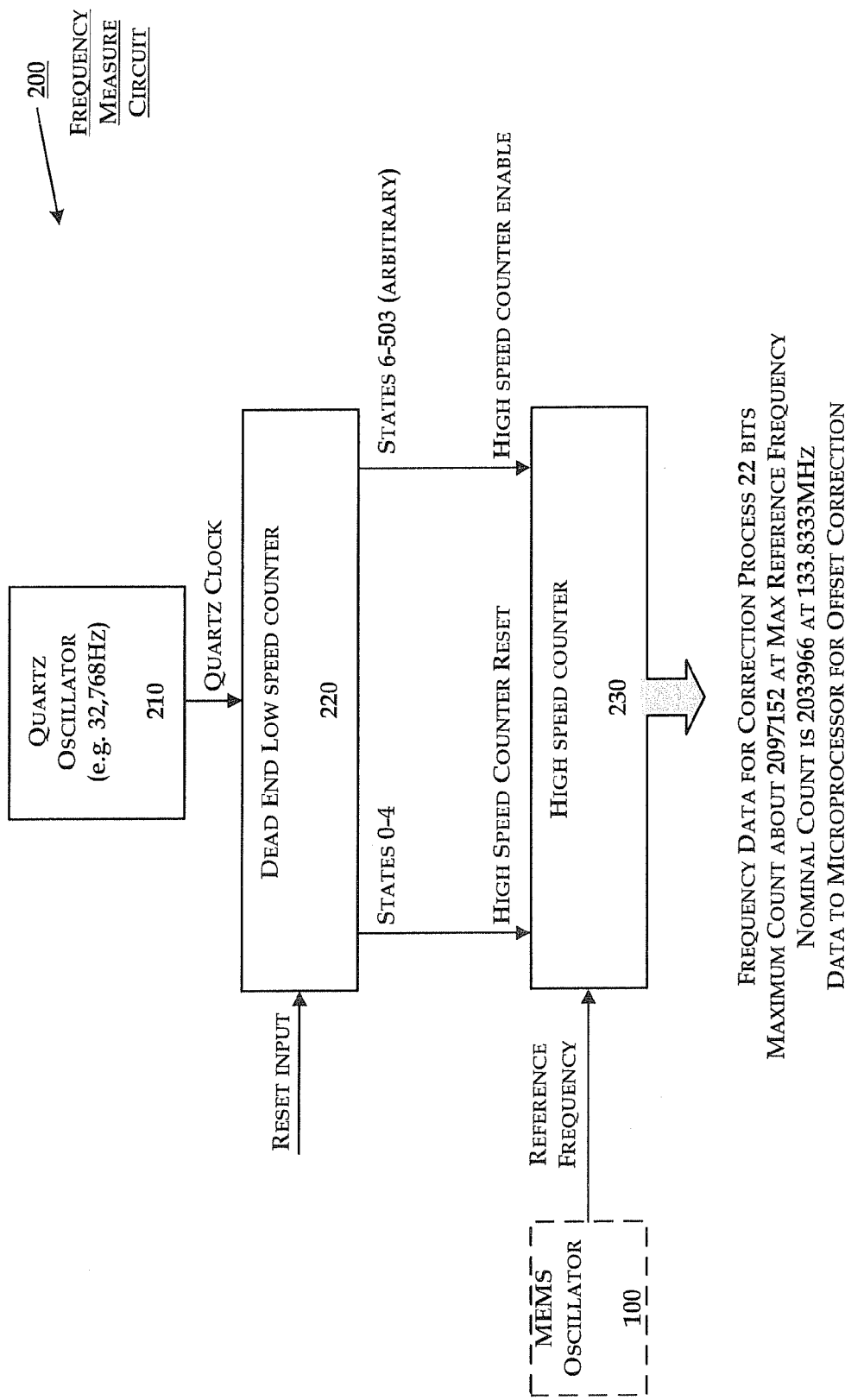
FIG. 2 shows an example quartz oscillator circuit configured for use in measuring the frequency of a MEMS type of oscillator circuit.

FIG. 2 shows an example quartz oscillator circuit configured for use in measuring the frequency of a MEMS type of oscillator circuit in accordance with at least some embodiments described herein. As illustrated, a quartz oscillator 210 is configured to generate a quartz clock such as, for example, from a tuning fork crystal with a frequency of about 32,768 Hz. The quartz clock serves as an input to a low speed counter 220 that is periodically reset (e.g., just prior to initiating a measurement). The outputs of the low speed counter correspond to various states or count values that are coupled as inputs to a high speed counter 230. The high speed counter 230 is operated from an oscillation or clock signal that has a characteristic reference frequency associated with the output of the MEMS oscillator 100.

The quartz oscillator 210, low speed counter circuit 220, and high speed counter circuit 230 are configured to collaboratively measure the frequency (i.e., reference frequency) of the MEMS oscillator 100. The high speed counter 230 is initially reset based on some count of the quartz oscillator 210 (e.g., states 0 to 4, for example), and the high speed counter is subsequently enabled based on a gated value (e.g., an arbitrarily selected value from states 6 through 503, for example) from the output of the low speed counter 220. After about $\frac{1}{128}$ of a second, roughly a million clocks of the MEMS oscillator 100 may be counted and the counting gate can be closed on the high speed counter 230 such that the count can be evaluated.

A processor such as a microcontroller or microprocessor can be adapted to evaluate the results of the high speed counter 230 and converts the count data to a correction value for used by a receiver or transmitter in receiving and/or transmitting communication signals with increased carrier frequency accurately. In some examples, the processor may be as is described with respect to FIG. 7. In some further examples the receiver/transmitters may be used in implanted medical devices such as a bionic implant that may be required to transmit/receive communication signals with relatively high accuracy and low power.

Figure 3:
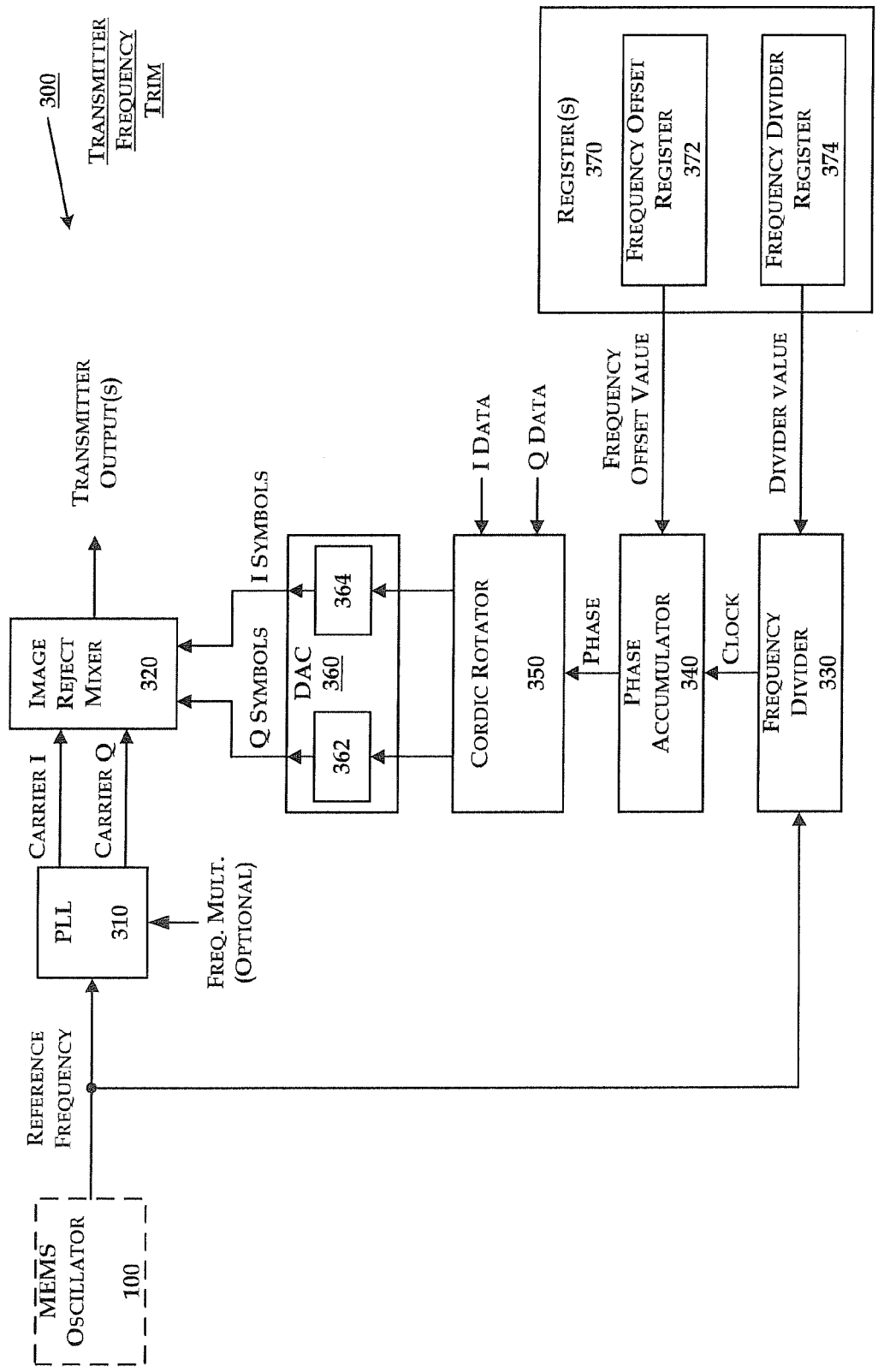
FIG. 3 is a schematic diagram of an example scheme for digitally compensating a transmit carrier frequency in an example system.
Figure 4:
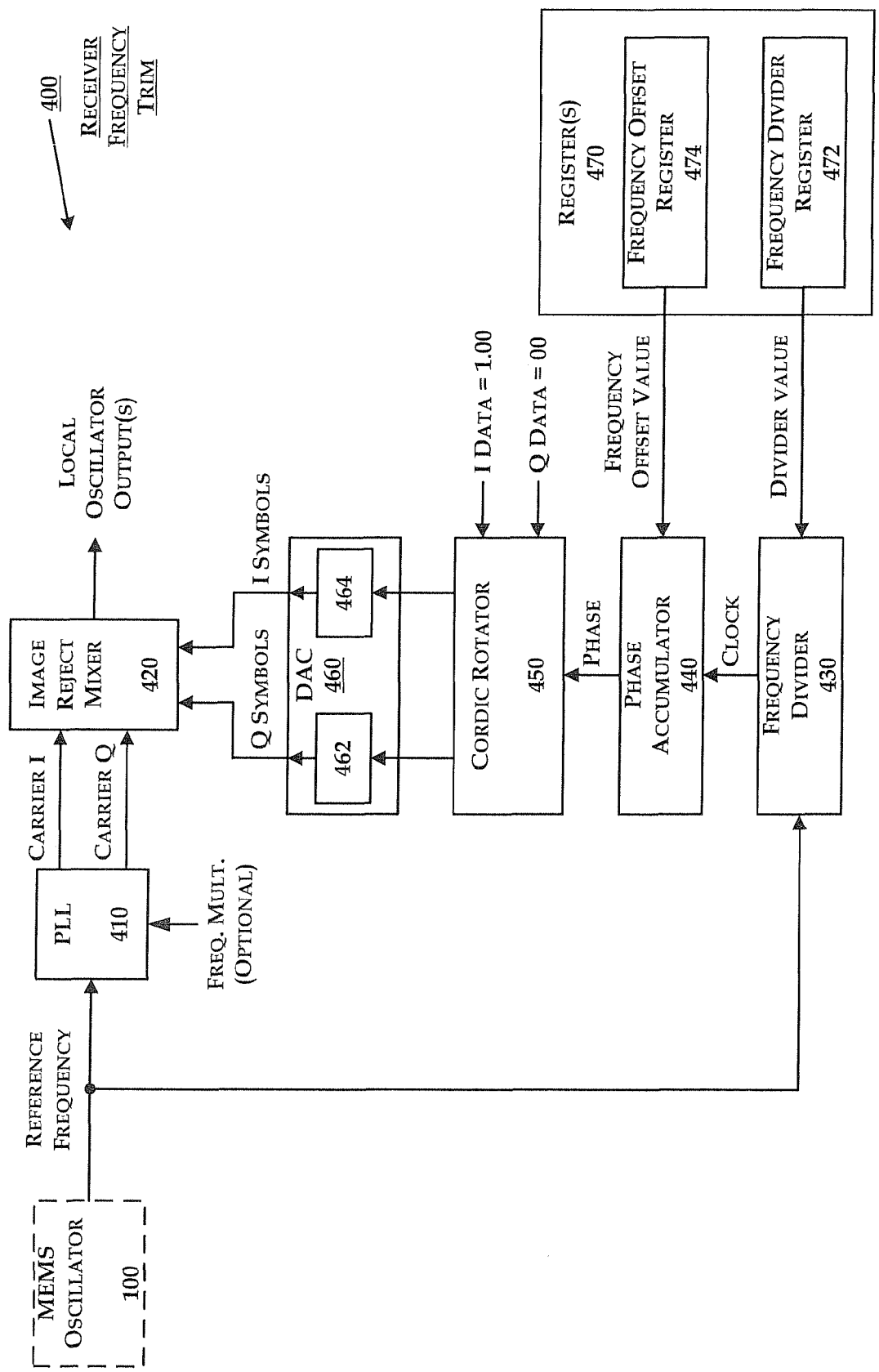
FIG. 4 is a schematic diagram of an example scheme for digitally compensating a receive carrier frequency in an example system.

FIG. 3 is a schematic diagram of an example scheme for digitally compensating a transmit carrier frequency in an example system arranged in accordance with the present disclosure. FIG. 4 is a schematic diagram of an example scheme for digitally compensating a receive carrier frequency in an example system arranged in accordance with the present disclosure. Both of these arrangements use a complex digital signal to frequency translate the MEMS frequency to the correct value, including, of course, any frequency multiplication or division that may be involved.

Example Receiver/Transmitter Trim Topologies

As shown in FIG. 3, a transmitter frequency trim topology 300 may include one or more of a phase locked loop 310, an image reject mixer 320, a frequency divider 330, a phase accumulator 340, a cordic rotator 350, a digital to analog converter 360 and one or more registers 370. A MEMS oscillator 100 can be coupled to PLL 310 and frequency divider 330. PLL 310 can also be coupled to image reject mixer 320. Register 372 can be coupled to phase accumulator 340. Register 374 can be coupled to frequency divider 330. Phase accumulator 340 can be further coupled to cordic rotator 350. Cordic rotator 350 can be further coupled to DAC 360. DAC 360 can be coupled to the image reject mixer 320.

MEMS oscillator 100 is adapted to provide an oscillation signal (or clock signal) with a corresponding reference frequency to PLL 310 and frequency divider 330. PLL 310 is configured to lock to the phase of the reference frequency and generate carrier signals for in-phase (I) and quadrature signals (Q), where the locked frequency can be adjusted to any other optional frequency multiplication factors. The carrier signals (I, Q) from PLL 310 are provided to image reject mixer 320, which is also configured to receive symbols (I, Q) from DAC 360. The image reject mixer generates the various transmitter output signals that include the I and Q symbols encoded into the I and Q carrier signals.

Frequency divider 330 is adapted to generate a clock based on the reference frequency from MEMS oscillator 100 and any divider value that may be provided by one of the registers. For example, registers 370 may include a frequency divider register 374 that is configured to store/retrieve a divider value that can be used by frequency divider 330 in generating the clock signal (CLOCK).

Phase accumulator 340 is configured to receive the clock signal (CLOCK) from frequency divider 330 and generate a phase signal (PHASE) that indicates an amount of accumulated phase error between the reference frequency and the desired oscillator frequency that was not achieved due to inaccuracy in the MEMS oscillator 100. Phase accumulator 340 references the phase error based on a frequency offset value that may be provided by one of the registers. For example, registers 370 may include a frequency offset register 374 that is configured to store/retrieve a frequency offset value that can be used by phase accumulator 340 in generating the phase signal (PHASE).

Cordic rotator 350 is configured to receive in-phase and quadrature (I, Q) data for transition from another circuit or register (not shown). The cordic rotator is configured to generate rotated symbols from the I and Q data using the accumulated phase error (PHASE) as a reference for rotation.

DAC 360 is configured to receive rotated I and Q data from cordic rotator 350, and generate complex analog symbols (I, Q Symbols) to the image reject mixer 320. DAC 360 may include separate DAC circuits for each of I and Q symbols as is illustrated by DAC 362 and DAC 364. The complex analog symbols from DAC 360 correspond to digital-to-analog converted version of the complex rotated symbols from cordic rotator 350.

As shown in FIG. 4, a receiver frequency trim topology 400 may include one or more of a phase locked loop 410, an image reject mixer 420, a frequency divider 430, a phase accumulator 440, a cordic rotator 450, a digital to analog converter 460 and one or more registers 470, 472 and 474. Register 472 in the receiver frequency trim section is connected to frequency divider 430 in a way similar to the operation of the transmitter trim section. Register 474 is connected to phase accumulator 440. DACs 462 and 464 are driven by the output of cordic rotator 450, and in turn connect to an image reject mixer 420. The operation of the receiver frequency trim is substantially similar to the operation of the transmitter frequency trim described above, except that the data input to the cordic rotator has a fixed value of 1 for the in-phase and 0 for the quadrature phase such that the image reject mixer effectively generates local oscillator output signals for the receiver operation. The operation will become more apparent from the discussion below.

Example Frequency Trim

As an example, suppose the system is designed to operate on the medical MIX band, at a frequency of about 401.5 MHz. A MEMS resonator (oscillator) can be designed to operate with a nominal frequency of about ⅓ of the 401.5 MHz frequency, or a design value of about 133.8333 MHz. However, conventional silicon resonators don't typically have such a tight tolerance on resonant frequency and tend to have inadequate trimming available to increase the accuracy. Thus, it is likely that a coarse MEMS resonant frequency will be achieved with an inaccuracy that may result in higher or lower frequencies than the designed resonant frequency. Moreover, the operating temperature of the MEMS device may result in further changes in the resonant frequency. For example, suppose the MEMS device actually resonates at a frequency of 134.2901223 MHz, which is too high by about 456.789 KHz at a certain temperature (with about 20 ppm/degree C. frequency coefficient). The frequency inaccuracy can either be periodically measured during operation so that the frequency can be corrected for transmitter/receiver operation, or the frequency inaccuracy can be stored in a lookup table or other contrivance that can be accessed during operation to provide for the frequency correction factors. For the example counter topology described in FIG. 2, the measurement of the frequency of the MEMS oscillator is a gated count whose gate time is controlled by a counter running from the 32,768 Hz quartz oscillator.

In some examples, the reference frequency from the MEMS oscillator 100 (or resonator) can be divided by a frequency divider value (e.g., by frequency divider circuit 330/430) for purposes of generating a clock signal (e.g., CLOCK in FIG. 3 or 4). The clock signal can then be coupled to a frequency compensation digital oscillator (e.g., the combined operation of phase accumulator 340/440 and/or cordic rotator 350/450), which can use positive or negative feedback to generate complex signals. For example, the clock signal with the frequency divided value can be used to clock a frequency compensation digital oscillator (e.g., a 16-bit digital oscillator). Since the digital oscillator is clocked by the divided reference frequency of the MEMS oscillator, frequency compensation can be realized. The appropriate adjustment count or adder/subtractor value for frequency compensation (e.g., Frequency Offset Value) can be determined by a counter value that is dependent on the desired oscillator/clock frequency and the amount of error in the measured frequency. For example, given a crystal oscillator with a frequency of 32,768 Hz and a MEMS oscillator with an ideal oscillating frequency of 133.8333 MHz and an actual oscillating frequency of 134.2901223 MHz (an error of 456.789 KHz), the frequency offset adjustment identified by a 16-bit counter can be determined as follows:

Count=$(2^{16})$·(Frequency Division Factor)·(Frequency Error)/(Measured Freq.)

or

Count=(65536)·(64)·(−456.789 KHz)/(134.2901223 MHz)=−14267.

The above described frequency offset adjustment methodology can set the carrier frequency of the receiver/transmitter to the correct frequency within a few hertz, which is adequate for most communications.

Example low power applications that may benefit from the described frequency trim methods may include biomedical devices such as implanted biomedical devices that are operated with very little power to prolong their useful life. The frequency measurements and adjustments described above can be achieved with very low power means, and with substantially no loop settling time requirement. For example, despite having a high Q, the MEMS oscillator 100 can be biased into operation quickly (e.g., on the order of microseconds) with a resonant frequency on the order of 133 MHz or so, and an example crystal oscillator 210 can run continuously on very low power (e.g., on the order of 10's of nanoamperes). In some example low power applications such as implanted biomedical devices, communications may be required on very low power. For example, a receiver/transmitter in an implanted biomedical device may be operated with a duty cycle on the order of about 100 micro-seconds per 2 seconds, with an oscillator current on the order of a few milli-amperes, a carrier frequency setting current of about 4 milli-amperes times 0.00005, or about 200 nanoamps. This power consumption is very low, likely orders of magnitude less than prior devices that use high frequency crystals, and offers potentially better frequency stability and lower phase noise. Furthermore, the described frequency trim topologies are likely more effective than prior devices that do not use crystal resonators, which tend to rely on fairly sensitive (e.g., "twitchy") and unstable signaling mechanisms. If the data rate of the transmitter/receiver is the order of a few hundred kilobits/second, and the data payload is on the order of 20 bits, then the time and current estimates described above should be adequate for low power operation with reasonable frequency accuracy.

Example Process Flows

Figure 5:
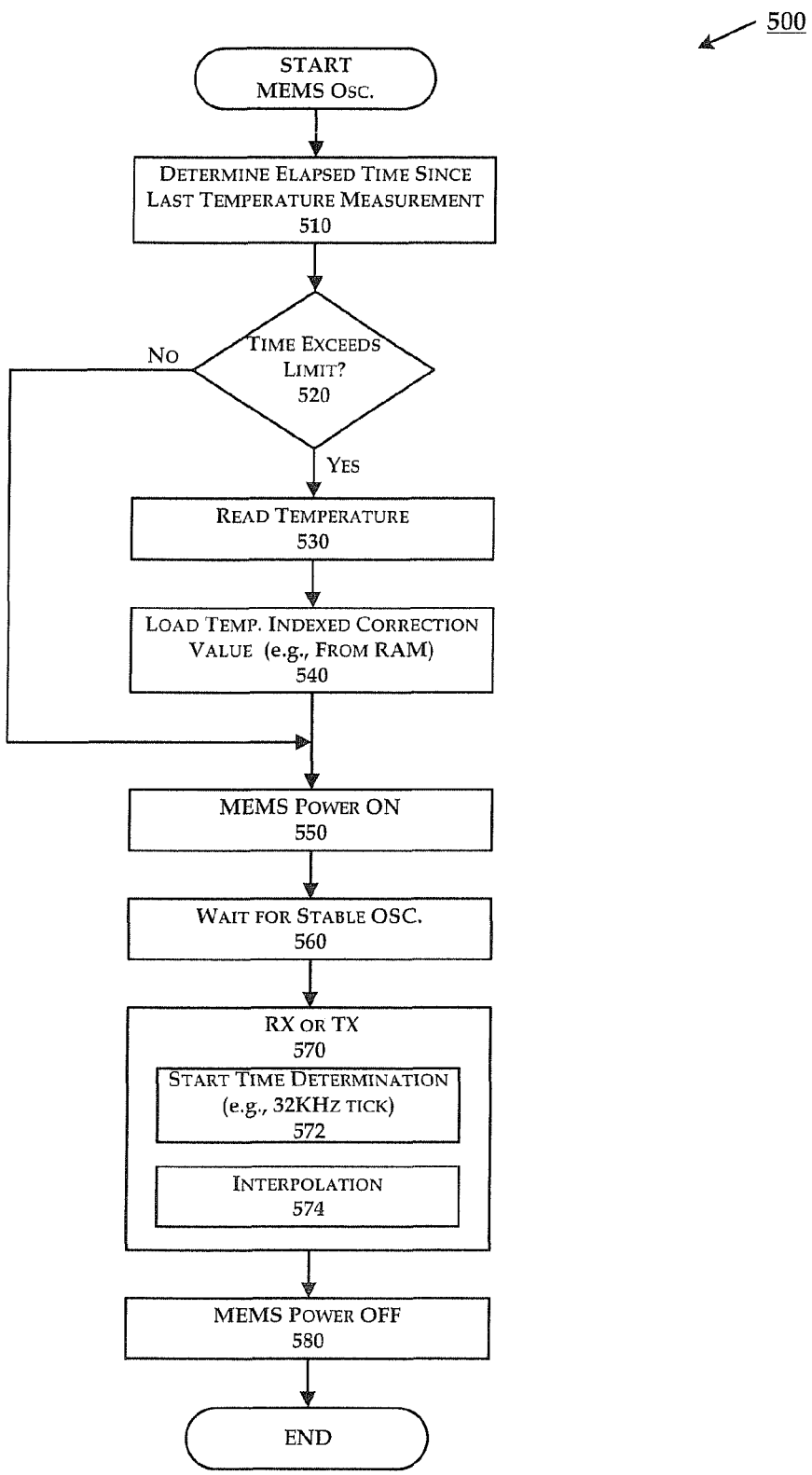
FIG. 5 is a flow chart of an example process for using temperature indexed correction factors in transmitter/receiver offset correction.

FIG. 5 is a flow chart of an example process 500 for using temperature indexed correction factors in transmitter/receiver offset correction, in accordance with at least some embodiments of the present disclosure. Process 500 may include one or more actions, functions, or operations as is illustrated by one or more of blocks 510 through 580. One or more of the described blocks may be implemented in hardware, software, or a combination thereof, including but not limited to any of the circuits or devices described with respect to FIGS. 1-4, and 7. Process 500 may begin at block 510.

At block 510, "DETERMINE ELAPSED TIME SINCE LAST TEMPERATURE MEASUREMENT", the system can be configured to determine how much time has elapsed since the last temperature measurement was made. In some examples a timer such as a countdown timer or interrupt timer can be configured to alert a processor to perform another temperature measurement. Block 510 may be followed by decision block 520.

At decision block 520, "TIME EXCEEDS LIMIT?", the system can be configured to determine if the time limit has been exceeded before another temperature measurement should be made. In some examples, digital logic such as from an interrupt timer or counter can be used to alert a processor when the time limit has been exceeded. In other examples, a processor may include facility to evaluate a counter value internal to the processor and determined if the counter value has exceeded some predetermined time limit. Decision block 520 may be followed by block 530 when the time limit is determined to have been exceeded. Alternatively, decision block 520 may be followed by block 550 when the time limit is determined to not have been exceeded.

At block 530, "READ TEMPERATURE", the system can be configured to determine the temperature associated with the system and/or the MEMS oscillator circuit. The temperature may be determined from any appropriate temperature sensor such as thermal diodes that may be implemented on a micro-chip, etc. The temperature measurement can be determined by single-ended or differential temperature measurements, or any other appropriate temperature measurement mechanism. Block 530 may be followed by block 540.

At block 540, "LOAD TEMP. INDEXED CORRECTION VALUE", the system can be configured to retrieve a previously determined temperature correction value such that frequency compensation/adjustment can be effectuated. For example, registers (or RAM, ROM, EPROM, flash RAM, etc.) can be accessed to retrieve a frequency offset value as was described previously concerning FIGS. 3 and 4. Each of the frequency offset values can be keyed off of a temperature index. In some examples, a frequency offset value for a particular temperature value may not be known, and an estimation of the appropriate frequency offset value can be determined (e.g., by interpolation between other values). Block 540 may be followed by block 550.

At block 550, "MEMS POWER ON", the system can be configured to activate the MEMS oscillator circuit. For example, the power to the electronics (e.g., 120, 130, etc.) in the MEMS oscillator circuit 100 can be applied to begin oscillator operation, and/or a polarizing bias voltage can be applied to the MEMS device. Block 550 may be followed by block 560.

At block 560, "WAIT FOR STABLE OSC.", the system can be configured to wait until the MEMS oscillator circuit has achieved a stable oscillation frequency. For example, the timer can be configured to indicate that a predetermine time interval has elapsed long enough that stable oscillation can be presumed. In some other examples, the frequency measure circuit can evaluate the MEMS oscillator 100 and determine that the frequency error is within appropriate limits. Block 560 may be followed by block 570.

At block 570, "RX OR TX", the system can be configured to operate as either a receiver or transmitter. The transmission and/or reception modes can be effectively frequency such as previously described in connection with FIGS. 2 and 3. Block 570 may in some examples further include additional blocks 572 and/or 574. At block 574, "START TIME DETERMINATION", the start time of the transmitter and/or receiver can be determined based on a number of clock ticks (e.g., out of a 32,768 Hz clock) associated with a clock signal (e.g., see FIG. 2). At block 574, "INTERPOLATION," the precise start time (e.g., the precise capture/transmit time interval for communications) associated with the transmitter/receiver can be determined as an interpolation between clock ticks. The communication cycle is effectively operated with the MEMS oscillator using the correction factors previously described. Once the communications are completed (i.e., either the receiver or transmitter operations are done), block 570 may be followed by block 580.

At block 580, "MEMS POWER OFF", the system can be configured to deactivate the MEMS oscillator circuit. For example, the power to the electronics (e.g., 120, 130, etc.) in the MEMS oscillator circuit 100 can be gated off (e.g., via a digitally controlled switching circuit under control by a processor or circuit) so that the electronics are powered off and power is conserved. Processing may end after block 580.

Figure 6:
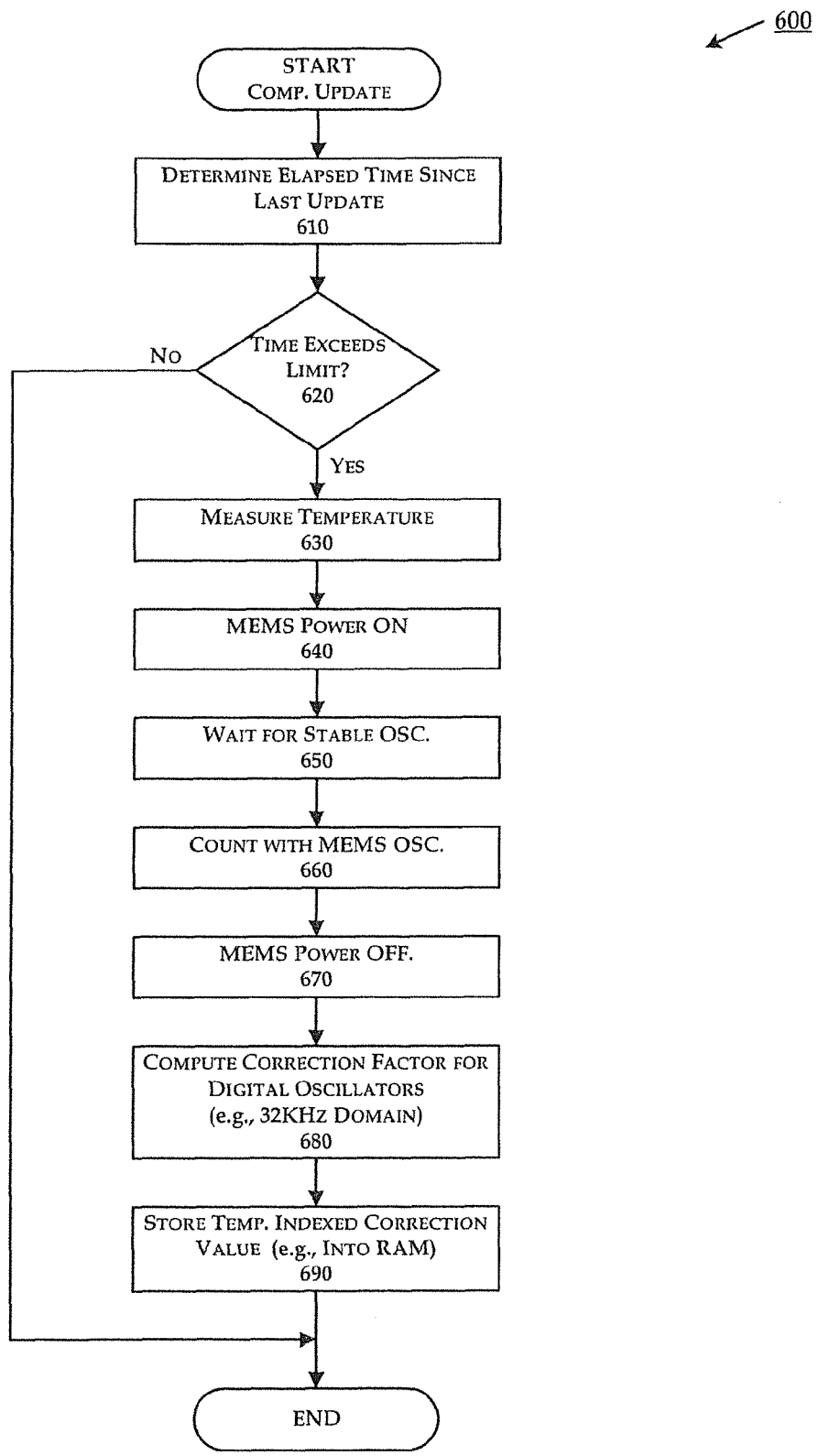
FIG. 6 is a flow chart of an example process for generating temperature indexed correction factors for use in transmitter/receiver offset correction.

FIG. 6 is a flow chart of an example process 600 for generating temperature indexed correction factors for use in transmitter/receiver offset correction, in accordance with at least some embodiments of the present disclosure. Process 600 may include one or more actions, functions, or operations as is illustrated by one or more of blocks 610 through 690. One or more of the described blocks may be implemented in hardware, software, or a combination thereof, including but not limited to any of the circuits or devices described with respect to FIGS. 1-4, and 7. Process 600 may begin at block 610.

At block 610, "DETERMINE ELAPSED TIME SINCE LAST UPDATE", the system can be configured to determine how much time has elapsed since the last temperature based correction factor was measured. In some examples a timer such as a countdown timer or interrupt timer can be configured to alert a processor to perform another temperature measurement. Block 610 may be followed by decision block 620.

At decision block 620, "TIME EXCEEDS LIMIT?", the system can be configured to determine if the time limit has been exceeded before another temperature measurement should be made. In some examples, digital logic such as from an interrupt timer or counter can be used to alert a processor when the time limit has been exceeded. In other examples, a processor may include facility to evaluate a counter value internal to the processor and determined if the counter value has exceeded some predetermined time limit. Decision block 620 may be followed by block 630 when the time limit is determined to have been exceeded. Alternatively, the update process may be concluded after decision block 620 when the time limit is determined to not have been exceeded.

At block 630, "MEASURE TEMPERATURE", the system can be configured to determine the temperature associated with the system and/or the MEMS oscillator circuit. The temperature may be determined from any appropriate temperature sensor such as one or more thermal diodes that may be implemented on a micro-chip, etc. The temperature measurement can be determined by single-ended or differential temperature measurements, or any other appropriate temperature measurement mechanism. Block 630 may be followed by block 640.

At block 640, "MEMS POWER ON", the system can be configured to activate the MEMS oscillator circuit. For example, the power to the electronics (e.g., 120, 130, etc.) in the MEMS oscillator circuit 100 can be applied to begin oscillator operation, and/or a polarizing bias voltage can be applied to the MEMS device. Block 640 may be followed by block 650.

At block 650, "WAIT FOR STABLE OSC.", the system can be configured to wait until the MEMS oscillator circuit has achieved a stable oscillation frequency. For example, the timer can be configured to indicate that a predetermine time interval has elapsed long enough that stable oscillation can be presumed. In some other examples, the frequency measure circuit can evaluate the MEMS oscillator 100 and determine that the frequency error is within appropriate limits. Block 650 may be followed by block 660.

At block 660, "COUNT WITH MEMS OSC.", the system can be configured to operate the counters to measure the frequency associated with the MEMS oscillator circuit relative to a clock signal. For example, the counters 220 and 230 in the frequency measurement circuit 200 can be operated with the quartz oscillator circuit 210 to count the number of clock ticks associated with the MEMS oscillator relative to the quartz clock signal from the quartz oscillator circuit 210. Block 660 may be followed by block 670.

At block 670, "MEMS POWER OFF", the system can be configured to deactivate the MEMS oscillator circuit. For example, the power to the electronics (e.g., 120, 130, etc.) in the MEMS oscillator circuit 100 can be gated off (e.g., via a digitally controlled switching circuit under control by a processor or circuit) so that the electronics are powered off and power is conserved. Block 670 may be followed by block 680.

At block 680, "COMPUTE CORRECTION FACTOR FOR DIGITAL OSCILLATORS", the frequency offset correction factor or value can be determined based on the difference between the expected frequency as a multiple of the low frequency clock (e.g., quartz oscillator 210) and the measured frequency from the MEMS oscillator 100. The offset determination may be as described previously in connection with FIG. 2. Block 680 may be followed by block 690.

At block 690, "STORE TEMP. INDEXED CORRECTION VALUE", the system can be configured to store a determined temperature correction factor or value such that frequency compensation/adjustment can be effectuated using the stored value. For example, registers can be accessed to store a frequency offset value as was described previously concerning FIGS. 3 and 4. Each of the frequency offset values stored in the register (or RAM, ROM, EPROM, flash RAM, etc.) can be keyed off of a temperature index. Processing may end after block 690.

Example Processor

Figure 7:
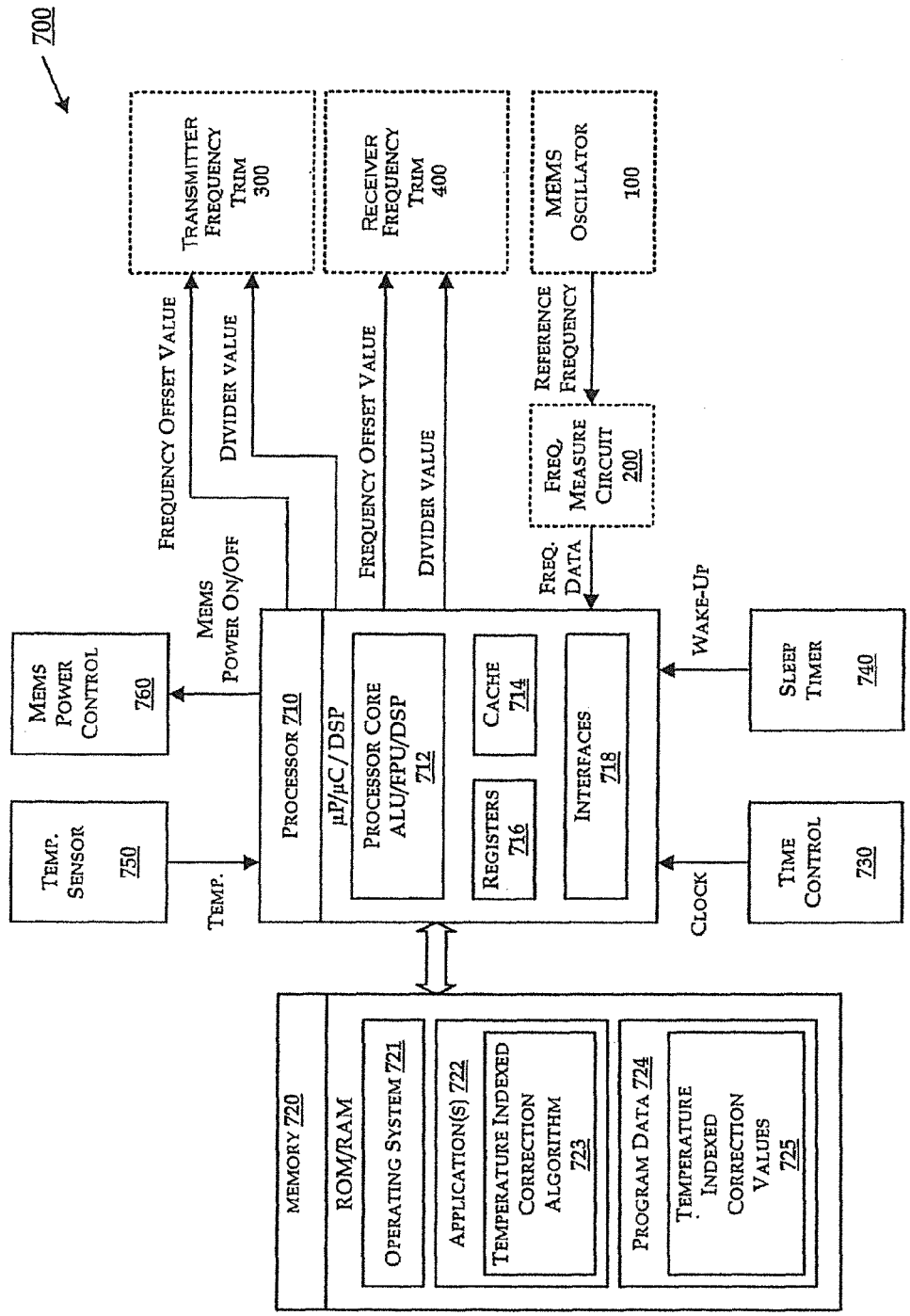
FIG. 7 is a block diagram of an example processor configured for facilitating various features described herein.

FIG. 7 is a block diagram of an example processor 700 or similar computing device configured for facilitating various features described herein. In a very basic configuration, processor 700 may include one or more processors 710 and memory 720. A bus may be used for communicating between the processor 710 and the memory 720.

Depending on the desired configuration, processor 710 may be of any type including but not limited to a microprocessor (μP), a microcontroller (μC), a digital signal processor (DSP), or any combination thereof. Processor 710 may include one or more levels of caching, such as a level one and/or a level two cache 714, a processor core 712, and one or more registers 716. The processor core 712 may include an arithmetic logic unit (ALU), a floating point unit (FPU), a digital signal processing core (DSP Core), or any combination thereof. Interfaces 718 such as a memory controller, an interrupt controller, a bus controller, a port interface or some other type of interface mechanism may also be used with the processor 710, or in some implementations the interfaces 718 may be an internal part of the processor 710.

Depending on the desired configuration, the memory 720 may be of any type including but not limited to volatile memory (such as RAM), non-volatile memory (such as ROM, EPROM, EEPROM, flash memory, etc.), or any combination thereof. System memory 720 may include an operating system 721, one or more applications 722, and program data 724. Applications 722 may include, for example, one or more temperature indexed correction algorithms or processes as described previously in connection with FIGS. 1-6. For example, the described applications may include processes/procedures to manage the activation/deactivation of power and/or circuitry, measure frequency offset correction values, store/retrieve frequency offset correction values, interpolate between frequency offset correction values, activate/deactivate neural stimulators, receive/transmit data with a receiver or transmitter device from an implant device to another device, etc. Program data 724 may include temperature indexed correction values 725 such as frequency offset values, and/or frequency divider values, data for communications such as I and Q data, all described previously.

Processor 200 may have additional features or functionality, and additional interfaces to facilitate communications between the basic configuration and any other required devices and/or interfaces. For example, processor 710 may be interfaced (e.g., via interfaces 718) with one or more of a time control circuit 730, a sleep timer circuit 740, a temperature sensor circuit 750, a MEMS power control circuit 760, a frequency measurement circuit 200, and/or one or more frequency trim circuits 300 or 400. The time control circuit can be adapted to generate a clock signal (CLOCK) as may be required for operation of processor 710, such as a crystal oscillator that may also be used for operation with the circuits of FIG. 2. The sleep timer 740 may be adapted to generate a wake-up signal (WAKE UP) based on some predetermined time interval such as via a countdown timer circuit, a count up timer circuit, or an interrupt circuit. The temperature sensor circuit 750, e.g., a temperature sensor such as thermally reactive diodes, etc., may be adapted to generate a temperature measurement signal (TEMP) such as may be useful for any of the described circuits and processes herein. The MEMS power control circuit 760 can be adapted to facilitate the activation and/or deactivation of MEMS Power (ON/OFF) such that at least those circuits illustrated in FIG. 1 can be selectively activated to conserve power. The frequency measurement circuit 200 is interfaced with the reference frequency from the MEMS oscillator 100 and also interfaced with the processor 710 such that the processor can evaluate and/or record frequency based measurements as previously described in connection with at least FIGS. 1-6. The various frequency trim circuits 300 and/or 400 can be further interfaced with processor 710 to facilitate communications of frequency offset values and/or divider values as is previously described.

One or more of the various processes including algorithms, operations, functions, procedures and/or methods described herein may be performed by the various systems and devices illustrated in at least FIG. 7. Moreover, the various processes may be stored on a data storage device, removable or non-removable storage devices, including but not limited to magnetic disk devices, flexible disk drives, hard-disk drives (HDD), optical disk drives such as compact disk (CD) drives or digital versatile disk (DVD) drives, solid state drives (SSD), and tape drives, to name a few. Example computer storage media may include volatile and/or nonvolatile, removable and/or non-removable media implemented in any method or technology for storage of information, such as computer readable instructions, data structures, program modules, or other data.

The computer storage media may be one example of a communication media. Communication media may typically be embodied by computer readable instructions, data structures, program modules, or other data in a modulated data signal, such as a carrier wave or other transport mechanism, and include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR), and other wireless media.

The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. An implanted medical device adapted for biological implantation, the implanted medical device including a radio frequency (RF) circuit for communication with an external unit or units, the medical device comprising:
a low frequency quartz oscillator circuit operative to generate a low frequency clock signal; a sleep timer circuit configured to periodically activate the implanted medical device from a sleep mode to an active mode; a MEMS resonator circuit having a characteristic resonant frequency, the MEMS resonator circuit being operative to generate an oscillator signal when the implanted medical device is operated in the active mode, the oscillator signal having a reference frequency corresponding to the characteristic resonant frequency of the MEMS resonator circuit; and a frequency compensated digital oscillator selectively operated with the oscillator signal from a MEMS oscillator circuit when the implanted medical device is operated in the active mode, the frequency compensated digital oscillator being configured to provide carrier frequency control and precision timing for the RF circuit using a measured frequency error of the reference frequency relative to the low frequency clock signal from the low frequency quartz oscillator circuit without frequency adjustment of the oscillator signal.

2. The implanted medical device of claim 1, where the low frequency quartz oscillator circuit is a quartz tuning fork resonator.

3. The implanted medical device of claim 1, where a carrier frequency for radio frequency communications is in a range from 100 MHz to 3000 MHz.

4. The implanted medical device of claim 1, wherein the sleep timer circuit is configured to intermittently operate the radio frequency circuit to conserve energy.

5. The implanted medical device of claim 1, further comprising a capacitive voltage multiplier adapted to deliver therapy to a nerve or tissue of a patient.

6. The implanted medical device of claim 1, further comprising an inductive voltage multiplier adapted to deliver therapy to a nerve or tissue of a patient.

7. The implanted medical device of claim 1, further comprising a charge pump circuit and a polarizing voltage source circuit, wherein the charge pump circuit is configured to generate an increased voltage signal when the implanted medical device is operated in the active mode, wherein the increased voltage signal is used to deliver therapy to a nerve or tissue of a patient, and wherein the polarizing voltage source circuit is adapted to power the MEMS resonator circuit using the increased voltage signal that is used for patient therapy.

8. The implanted medical device of claim 7, further comprising a neural stimulator circuit that is powered by the increased voltage signal from the charge pump circuit, wherein the neural stimulator circuit is configured to deliver therapy to the nerve or tissue of the patient when the implanted medical device is operated in the active mode.

9. The implanted medical device of claim 1, wherein the reference frequency of the MEMS resonator circuit is measured against a frequency of the low frequency quartz resonator.

10. The implanted medical device of claim 1, further comprising a temperature sensor circuit and a frequency measurement circuit, wherein the temperature sensor circuit is configured to measure a temperature of the implanted medical device, and wherein the frequency measurement circuit is configured to measure the reference frequency of the MEMS resonator circuit whenever the temperature of the implanted device is determined to vary from a previous temperature.

11. The implanted medical device of claim 1, wherein the frequency compensated digital oscillator is configured effective to adjust carrier frequency characteristics to compensate for manufacturing tolerances and variations in the reference frequency of the MEMS oscillator circuit.

12. The implanted medical device of claim 1, wherein the frequency compensated digital oscillator is configured effective to adjust carrier frequency characteristics to compensate for temperature variations in the reference frequency of the MEMS oscillator circuit.

13. The implanted medical device of claim 1, wherein the frequency compensated digital oscillator is digitally applied to either a transmit frequency correction, a receiver frequency correction, or both.

14. The implanted medical device of claim 1, further comprising a temperature sensor circuit configured to determine a temperature of the MEMS oscillator circuit, wherein the temperature is used to compute the frequency correction applied to the reference frequency, once initial measurements of the reference frequency and temperature have been made.

15. The implanted medical device of claim 1, where the MEMS oscillator circuit is used to provide a clock source for digital interpolation of timing between pulses of a low frequency quartz resonator.

16. The implanted medical device of claim 1, further comprising a frequency measurement circuit that is configured to measure the reference frequency of the MEMS oscillator circuit relative to the frequency of the low frequency clock signal from the low frequency quartz oscillator circuit.

17. The implanted medical device of claim 16, the frequency measurement circuit comprising a low speed counter and a high speed counter, wherein the low speed counter is configured to selectively operate from the low frequency clock signal of the low frequency quartz oscillator circuit and provide a count, and wherein the high speed counter is configured to operate from the oscillator signal and the count from the low speed counter such that the high speed counter counts for a number of clocks ticks associated with the oscillator signal from the MEMS oscillator circuit relative to a number of clock ticks associated with the clock signal from the low frequency quartz oscillator circuit.

18. The implanted medical device of claim 17, further comprising a processor configured to determine an offset correction factor based on counts determined by the frequency measurement circuit.

19. The implanted medical device of claim 1, further comprising a temperature sensor, a processor, and a register, wherein the temperature sensor is configured to measure a temperature associated with the implanted medical device, and wherein the processor is configured to retrieve a frequency offset value from the register based on an index associated with the measured temperature.

20. An implanted medical device that is adapted to deliver therapy to a nerve or muscle tissue of a patient and also configured for radio frequency communication with an external unit or units, the implanted medical device comprising: a low frequency quartz oscillator circuit configured to generate a low frequency clock signal; a sleep timer circuit that is adapted for operation with the low frequency clock signal and configured to periodically activate the implanted medical device from a sleep mode to an active mode; an on chip silicon MEMS resonator circuit that is configured to selectively generate an oscillator signal when the implanted medical device is operated in the active mode, wherein the oscillator signal has a reference frequency corresponds to a characteristic resonant frequency of the MEMS resonator circuit; and frequency compensation means selectively operated with the oscillator signal from a MEMS oscillator circuit when the implanted medical device is operated in the active mode, wherein the frequency compensation means provides carrier frequency control and/or precision timing for the radio frequency communications using a measured frequency error of the reference frequency relative to the low frequency clock signal from the low frequency quartz oscillator circuit, and also using a frequency compensation factor without frequency adjustment of the oscillator signal.

* * * * *